United States Patent [19]
Forestiere et al.

[11] Patent Number: 6,149,879
[45] Date of Patent: Nov. 21, 2000

[54] MODULAR DEVICE THAT COMPRISES A REACTION ZONE AND A SEPARATION ZONE

[75] Inventors: Alain Forestiere, Vernaison; Quentin Debuisschert, Rueil Malmaison; Isabelle Harter, Lyons; Jean-Paul Dessapt, Beynes; Pierre Marache, Rueil Malmaison, all of France

[73] Assignee: Institut Francais du Petrole, France

[21] Appl. No.: 09/022,842

[22] Filed: Feb. 12, 1998

Related U.S. Application Data

[60] Provisional application No. 60/040,575, Mar. 14, 1997.

[30] Foreign Application Priority Data

Feb. 12, 1997 [FR] France ................................. 97 01793

[51] Int. Cl.[7] .............................. B01J 10/00; C07C 41/05
[52] U.S. Cl. .......................... 422/191; 422/192; 422/193; 422/195; 568/697
[58] Field of Search ................................. 203/DIG. 6, 99; 261/146, 100; 422/191, 192, 193, 195; 568/697

[56] References Cited

U.S. PATENT DOCUMENTS

| | | | |
|---|---|---|---|
| 1,858,158 | 5/1932 | Laird | 261/114.1 |
| 2,877,099 | 3/1959 | Bowles | 422/195 |
| 4,089,752 | 5/1978 | Hancock, II | 203/99 |
| 5,013,407 | 5/1991 | Nocca et al. | 202/158 |
| 5,026,459 | 6/1991 | Quang et al. | 202/158 |
| 5,130,102 | 7/1992 | Jones | 422/191 |
| 5,308,592 | 5/1994 | Yang et al. | 422/191 |
| 5,338,517 | 8/1994 | Evans, III | 422/191 |

FOREIGN PATENT DOCUMENTS

| | | |
|---|---|---|
| 0 755 706 | 1/1997 | European Pat. Off. |
| 366519 | 2/1963 | Switzerland. |

*Primary Examiner*—Marian C. Knode
*Assistant Examiner*—Frederick Varcoe
*Attorney, Agent, or Firm*—Millen, White, Zelano & Branigan, P.C.

[57] ABSTRACT

The invention relates to a modular device that comprises a reaction zone that includes a catalyst bed and a zone for separation by distillation, as well as independent circulation channels for liquid fluid and gaseous fluid.

19 Claims, 3 Drawing Sheets

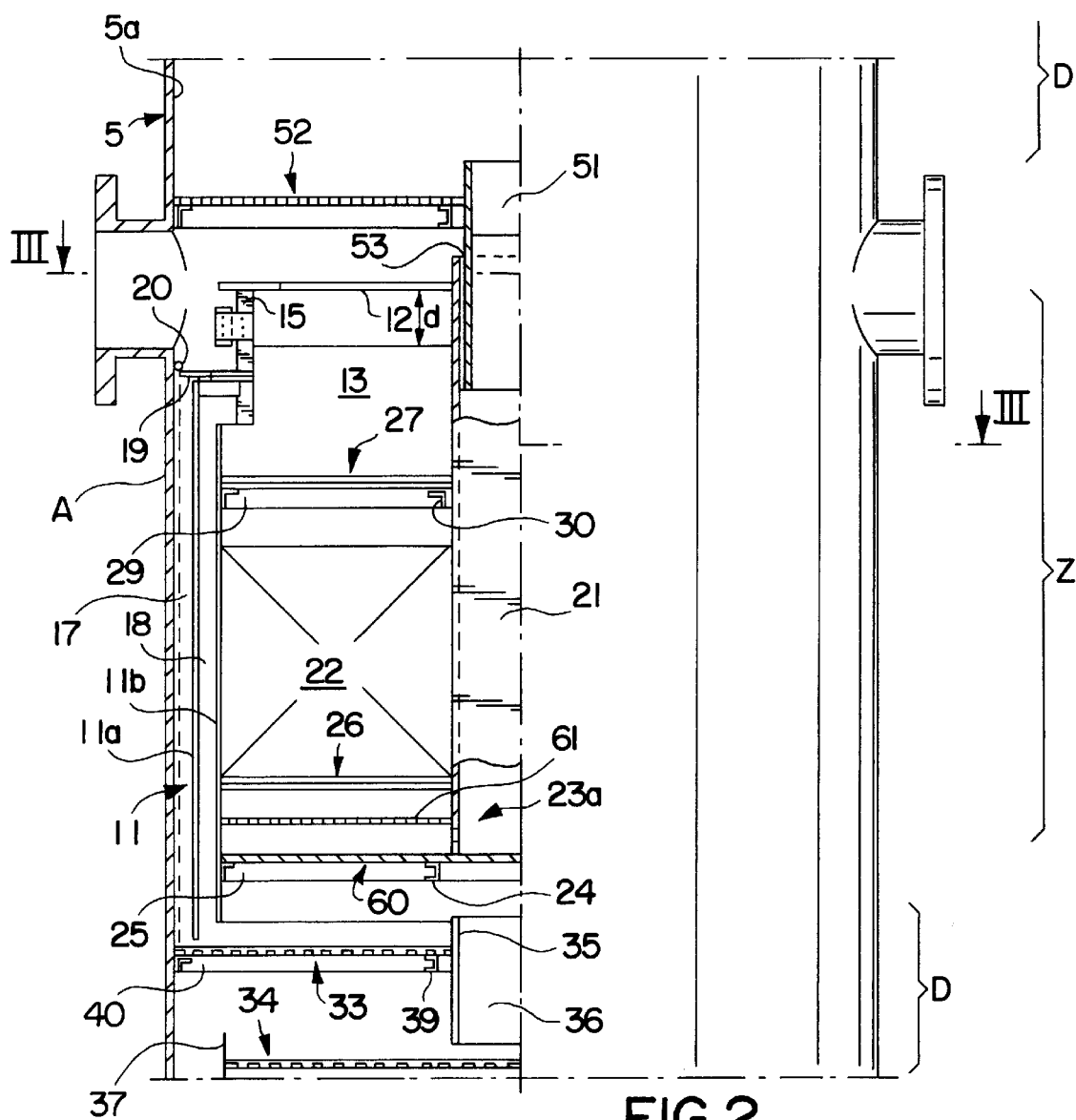
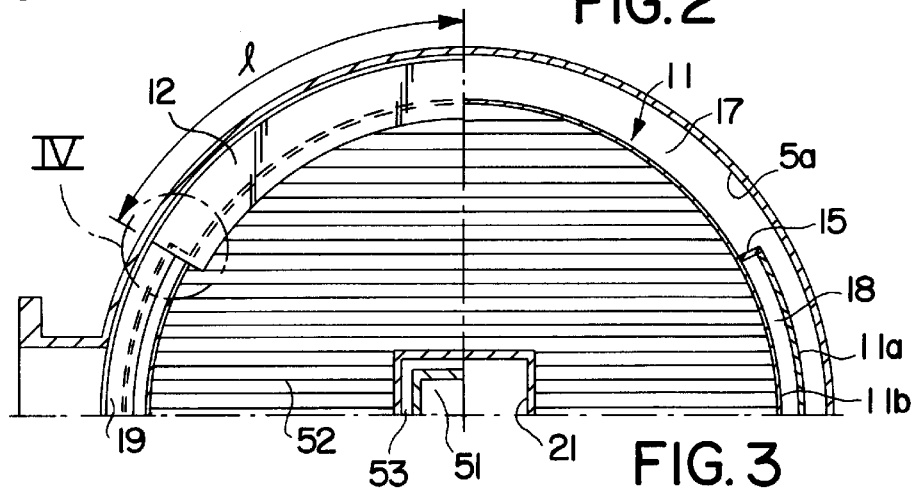
FIG.2
FIG.3

MODULAR DEVICE THAT COMPRISES A REACTION ZONE AND A SEPARATION ZONE

This application claims priority of provisional application 60/040,575 filed Mar. 14, 1997 under the provisions of 35 U.S.C. 119(e).

The invention relates to a device that makes it possible to carry out at least one chemical reaction, which may or may not be balanced, in the presence of a catalyst.

According to an embodiment, the device according to the invention makes it possible to carry out a chemical reaction followed by separation of the reaction mixture that is obtained.

The invention relates in particular to devices for reactive distillation, also called catalytic distillation.

The device according to the invention can be used to carry out various chemical reactions, which may or may not be balanced, for example, in the liquid phase, for which the reaction product is isolated by distillation, under the temperature and pressure conditions under which the reaction is carried out.

The device is particularly well suited for use in the preparation of tert-alkyl ethers such as methyl tert-butyl ether (MTBE), methyl tert-amyl ether (TAME), ethyl tert-butyl ether (ETBE) or else ethyl tert-amyl ether (TAEE), by catalytic reaction on the suitable olefin (isobutene or isopentene) of the suitable alcohol (methanol or ethanol as appropriate). With regard more particularly to etherification reactions by reactive distillation, various processes have already been proposed in the prior art.

The devices that are described in the prior art for carrying out this type of reaction (a balanced chemical reaction in the presence of a catalyst) comprise one or more zones in which a catalytic reaction and separation by distillation of the products of said reaction are carried out concurrently, whereby this zone comprises at least one reaction plate that supports a particular catalyst and at least one distillation plate for, e.g., separation by distillation.

In the majority of devices or reactors of the prior art such as those described in Patents FR-2,628,148, FR-2,628,737, FR-2,684,893, FR-2,737,131, FR-2,737,132 of the applicant, the various elements that form the reactive distillation column are integral with one another and are fastened to the walls of the reactor, thus making the structure rigid. Maintaining such a reactor proves to be relatively difficult and expensive, particularly because of the presence of this fixed connection between the various elements that form the reaction zones and distillation zones and also with the column. Actually, in the case where just a single zone can no longer perform its function, it is necessary to modify all of the elements. Moreover, it proves difficult, if not impossible, to modify structures of existing columns to upgrade them or else to replace defective parts or zones.

The device according to the invention comprises a more flexible, modular-type structure, which makes it possible in particular to adapt the device easily to the needs of the producer and to upgrade it while in service, for example.

The invention is also used for remodeling existing columns or for "revamping" the unit.

In addition, a modular design of the device makes it possible advantageously to facilitate maintenance operations on each of its elements.

The device of the invention can be used to carry out various chemical reactions, which may or may not be balanced, in the liquid phase, for which the reaction product can be isolated by distillation under the temperature and pressure conditions under which the reaction is carried out. It can be used for alkylation reactions of aromatic hydrocarbons, generally benzene, by catalytic reaction with the suitable olefin, for example ethylene or propylene, to form the corresponding alkyl benzene, for example ethyl benzene or cumene. It can, however, also be used for, e.g., paraffin isomerization reactions, olefin isomerization reactions, or the production of butene-2 by hydro-isomerization of butene-1. It can also be used for the hydrogenation reaction of benzene and light olefins (that have at most 6 carbon atoms in their molecules) in the light reformate, or for the hydrogenation reaction of diolefins and/or acetylenic compounds in light fractions of petroleum or petrochemical fractions. Preferably, it is used for etherification reactions between an isoolefin (for example, isobutene and isopentene) and an aliphatic monoalcohol (such as methanol or ethanol), particularly in the preparation of tert-alkyl ethers such as methyl tert-butyl ether (MTBE), methyl tert-amyl ether (TAME), ethyl tert-butyl ether (ETBE) or else ethyl tert-amyl ether (TAEE), by catalytic reaction on the suitable olefin (isobutene or isopentene) of the suitable alcohol (methanol or ethanol, as appropriate).

This invention relates in particular to a modular device that makes it possible to carry out at least one chemical reaction, which may or may not be balanced, in the presence of a catalyst that comprises in combination:

at least one reaction zone where the chemical reaction is carried out, whereby the zone comprises a chamber where a catalyst bed that comprises the catalyst is located, means for introducing a basically liquid fluid $F_1$ or $F_2$ that contains at least the reagent or reagents, whereby the means are located approximately in the center of the chamber, with the introduction being carried out without there having to be any contact with the catalyst and up to the catalyst, one or more sections for passage of a second fluid $F_2$ that comprises reagents and the products that come from the catalyst, whereby the fluid is basically liquid, one or more sections for passage that allows the circulation of at least a third fluid $F_3$ that is basically gaseous, the sections for passage are dedicated to the passage of a fluid, a section for passage comprises at least one lateral wall that is common with a section for passage, and at least one wall that is formed by the inner wall of a reactive distillation device or an auxiliary element, the sections for passage are distributed over at least a portion of the periphery of the central chamber.

The sections for passage that are dedicated to the passage of basically liquid fluid are formed by, for example, a double wall, whereby one of the walls is common to at least a portion of the outer wall of the chamber.

The means that allow the distribution of basically liquid fluid comprise, for example, a pipe that is equipped with one or more orifices that communicate with a distribution zone that is located below the catalyst bed.

The distillation zone comprises, for example, at least one lower airtight plate and at least one perforated plate, whereby the plates are separated by a distance 'h.'

The perforated plate comprises, for example, several sectors for distribution of a basically liquid fluid, whereby the sectors are separated by means and each of the sectors communicates with at least one opening of the pipe.

The pipe is equipped with, for example, an element that makes it possible to keep the catalyst bed from clogging and to deflect excess liquid toward a channel for circulation of the liquid.

According to the invention, the device is linked to, for example, at least one distillation zone D, whereby the distillation zone communicates with the reaction zone through circulation channels.

This invention also relates to a column that makes it possible to carry out at least one chemical reaction, which may or may not be balanced. It is characterized in that it comprises at least one modular device that makes it possible to carry out at least one chemical reaction, which may or may not be balanced, in the presence of a catalyst that comprises in combination:

at least one reaction zone where the chemical reaction is carried out, whereby the zone comprises a chamber where the catalyst is located, means for introducing a basically liquid fluid $F_1$ or $F_2$ that comprises at least the reagent or reagents, whereby the means are located approximately in the center of the chamber, with the introduction being carried out without there having to be any contact with the catalyst and up to the catalyst, one or more channels for circulation of a second fluid $F_2$ that comprises reagents and the products that come from the catalyst, whereby the fluid is basically liquid, one or more channels for circulation that allows the circulation of at least a third fluid $F_3$ that is basically gaseous, the channels for circulation are dedicated to the passage of a fluid, a circulation channel comprises at least one lateral wall that is common with a circulation channel, and at least one wall that is formed by the inner wall of a reactive distillation device or an auxiliary element, said channels for circulation are distributed over at least a portion of the periphery of said central chamber, and at least one distillation zone D, whereby the distillation zone communicates with the modular device via the circulation channels.

The modular device is located, for example, between an upper distillation zone and a lower distillation zone.

The modular device is suspended, for example, in the inner wall of the column.

Means are located, for example, between the modular device and the inner wall of the column to keep fluid $F_3$ from meeting fluid $F_2$ outside of the distillation zones.

The means of introduction can communicate with a distribution device that is located below the catalyst, whereby the means and the device are selected to make it possible to circulate fluid $F_2$ or $F_1$. from the top to the bottom up to the distribution device and to ensure upward circulation inside the catalyst.

Fluid $F_2$ or $F_1$ circulates, for example, in a downward manner outside the catalyst, and fluid $F_3$ circulates, for example, in an upward manner in the circulation channel.

The column and the modular device according to the invention will advantageously be used to carry out the synthesis of tert-alkyl ethers, such as methyl tert-butyl ether (MTBE), methyl tert-amyl ether (TAME), ethyl tert-butyl ether (ETBE) or else ethyl tert-amyl ether (TAEE), by catalytic reaction on the suitable olefin (isobutene or isopentene) of the suitable alcohol (methanol or ethanol as appropriate).

BRIEF DESCRIPTION OF THE DRAWINGS

Other advantages and characteristics of this invention will become clearer from reading the description given below as embodiments, within the framework of applications that are by no means limiting, by referring to the accompanying drawings, where:

FIG. 2 represents a cutaway view of a doublet according to the invention, FIGS. 3 and 4 show, respectively, a section of the device of FIG. 2 and a detail of an example of means that make it possible to hold a doublet relative to a wall.

The following description is provided as illustrative and nonlimiting examples and relates to a reactive distillation column where a chemical reaction is carried out in the presence of a catalyst and a reaction is carried out for separation of the reaction mixture that is obtained by distillation.

In the description below, reference is made particularly to three types of fluids that are defined below:

$F_1$ is a basically liquid fluid that comprises one or more reagents, $F_2$ is a basically liquid fluid that comprises excess reagents that have not reacted in the catalyst and the products that come from the catalytic reaction, and $F_3$ is a basically gaseous fluid or vapor that comprises the products that come from the catalytic reaction.

Figure 1:
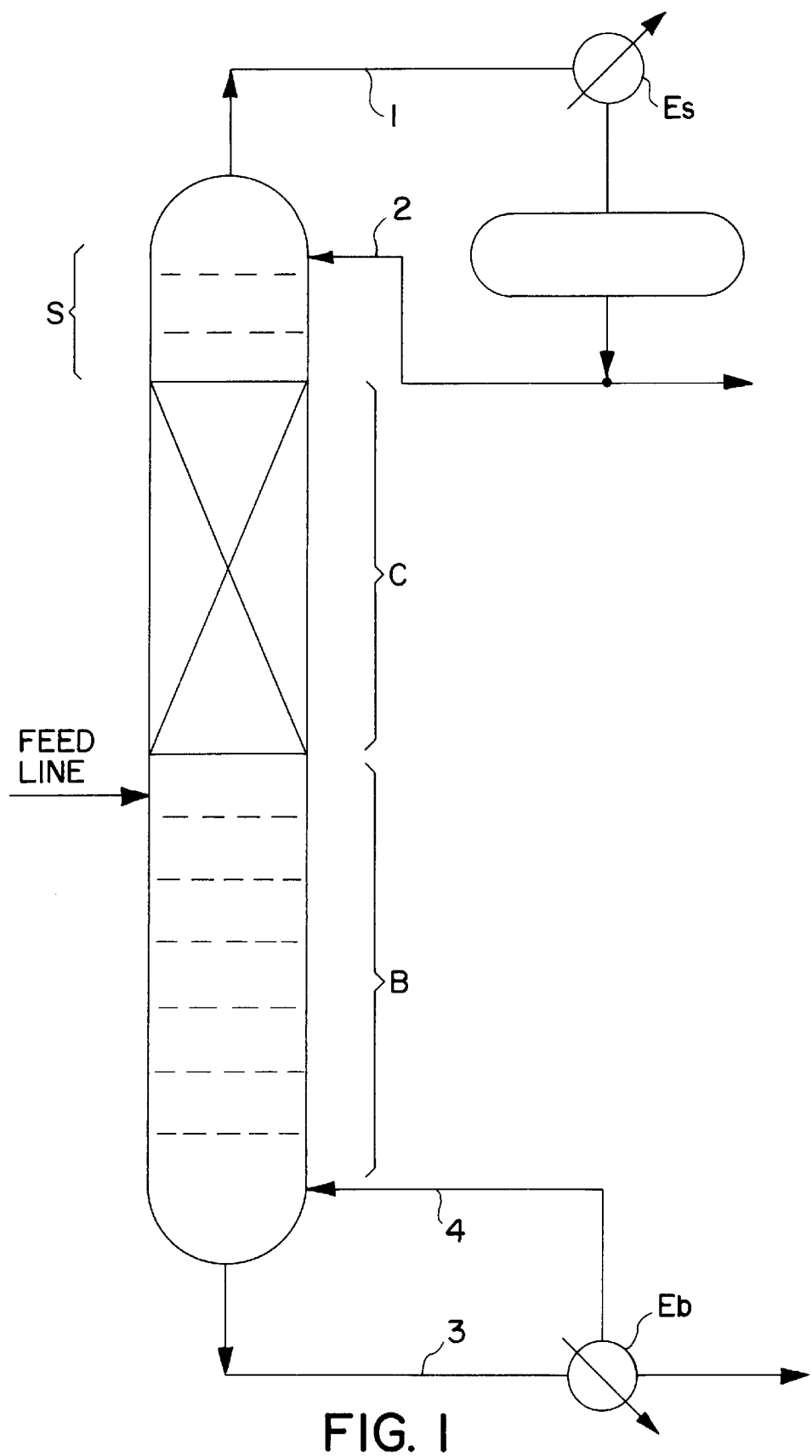
FIG. 1 shows an embodiment of a column that comprises at least one modular element that comprises a reaction zone and a distillation zone that are separate and that have the characteristics according to the invention.

FIG. 1 shows a diagram of a reactive distillation column that is usually used and that comprises, for example, three zones, a catalytic zone C in which are performed the chemical reaction and the separation, for example by distillation, in separate zones (respectively referenced R and D), a top or rectification zone S, and a base or drainage zone B.

Top S is equipped with, for example, a pipe 1 or line for evacuating vapors from the most volatile components and a pipe 2 that makes it possible to introduce a liquid fraction that is formed by, for example, at least one fraction of the vapors that are condensed in exchanger Es.

At base B are a line 3 or pipe that makes it possible to evacuate the least volatile components in liquid form and a line 4 that makes it possible to introduce a vapor fraction that is generated by, for example, partial vaporization of at least a portion of the components in exchanger Eb. Said base is also equipped with one or more pipes for the optional introduction of all or part of the reagents.

Internally catalyst zone C receives a liquid phase that is generated by the reflux that is introduced at the reactive distillation zone and a vapor phase that is generated by the boiling vapor that is introduced at, for example, the distillation base.

Externally it is also possible to introduce at, for example, at least one level, a possible input of at least one of the reagents, pure or diluted with, for example, alcohol, in the case where the ether synthesis device is used, whereby this variant embodiment is not shown in the figure, or else the hydrogen in some particular cases of use, or any other liquid or gas chemical reagent is used under the conditions of the operation.

FIGS. 2 to 6 below show, in a detailed manner, an embodiment of the device according to the invention that is positioned in a reactive distillation column that is described in FIG. 1.

FIGS. 2 and 3 show, respectively, a cutaway view and, along a section III—III of FIG. 2, a unit or doublet that consists of a reaction zone Z that is located above a distillation zone D. The term doublet generally designates a unit that is formed by a reaction zone and one or two distillation zones D that are located above and below.

At its upper part, reaction zone Z can be connected to a means for introducing the fluid, which can also be considered as forming part of the distillation zone.

It can also be linked to a distillation zone D that is located above.

Reaction zone Z comprises, for example, a chamber 11 (FIG. 2) or central chamber inside of which is located the catalyst, which can be in the form of, for example, a catalyst bed 22. The composition of the catalyst and the form in which it is present are described in, for example, Patent FR 2,737,131 of the applicant, whose technical teaching is incorporated by reference.

On at least a portion of its periphery, chamber 11 comprises several passage sections that are referenced 17 and 18 (FIG. 3), which are dedicated to the passage for fluid $F_3$, which is present in vapor form, and of basically liquid fluid $F_2$ that comprises the products and the excess reagents that have not reacted. In this example, the reaction zone is located between two distillation zones D that comprise two double-pass distillation plates as presented in detail below. Inner wall 5a of the reactive distillation column will be used as a wall to delimit at least one of the channels for circulation of fluids $F_3$ or $F_2$.

Wall 11b of chamber 11 is equipped in its upper portion with a raised edge 12 that is located at a distance "d" from its upper portion 13, whereby the raised edge can extend over a length "1" of the periphery of chamber 11. This raised edge acts as a deflector for vapor $F_3$ that circulates in the upward direction and comes from lower distillation zone D.

Several elements 15, such as pieces of sheet metal, are located outside of wall 11b and extend over the length of chamber 11 in order to form the walls that delimit several paths of circulation for fluids $F_2$ and $F_3$ along the chamber and outside of the latter.

Two consecutive walls 15 are separated by, for example, a distance that corresponds to length "1" of the raised edge of deflection. Channel 17 for circulation of the vapor is delimited by inner wall 5a of the reactive distillation column, wall 11b of the chamber, and two walls 15, and raised edge 12 that is connected to, for example, two walls 15 will allow the deflection of the flow of vapor $F_3$ that circulates in flow channel 17.

To create a channel 18 for circulation of liquid, two walls 15 will be connected by a wall 11a which is spaced from wall 11b of the chamber and at wall 11b.

By positioning several raised edges 12 along the periphery of chamber 11 and several pieces of sheet metal 15, it is thus possible to create several circulation spaces or circulation channels for the vapor that comes from the distillation zone and by arranging several walls of type 11a, to generate several paths for circulation of the liquid. Various circulation channels 17 and 18 are distributed around wall 11b of chamber 11. The vapor passes virtually completely into a channel 17, while the liquid that comes from a catalyst bed circulates in a double-wall-type channel 18.

A piece of sheet metal 19 that is located between wall 11a and inner wall 5a of the reactive distillation column, and sealing means 20, such as seals, make it possible to deflect the vapor that rises toward circulation channels 17, thus keeping it from meeting with circulation of the liquid.

The passage of the liquid that comes from the catalyst bed toward a circulation channel 18 is presented in detail below.

The geometry and size of circulation channels 17 and 18 are selected to ensure good circulation of the fluids by reducing the losses of load, turbulence, or any other phenomenon that could affect the sequence of the chemical reaction and/or the flow of fluids.

Figure 4:
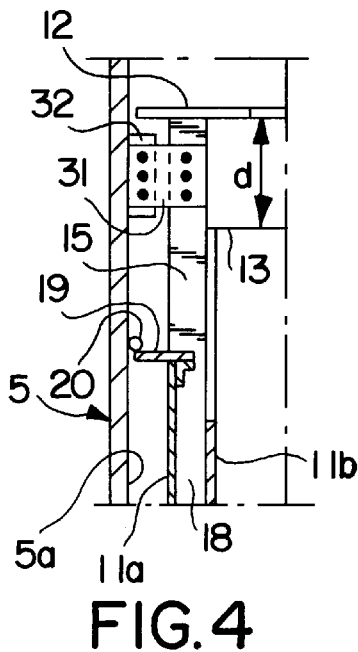

Chamber 11 that is equipped with various channels for circulation of vapor and liquid is mounted in the chamber of the reactor or column at, for example, its inner wall 5a with means for suspension or any other means that make it possible to install or quickly remove the unit, of which one example is given in FIG. 4 in an illustrative example.

Without exceeding the scope of the invention, another way to form the separate passage paths consists in adapting an auxiliary element that will act as the inner wall of the column. In an airtight manner, for example, an auxiliary unit A (not shown in the figures) is positioned relative to walls such as 5 to form circulation spaces 17. Such an embodiment makes the element more independent and does not require that it be inserted into a preexisting chamber or column.

Reaction zone Z can be equipped with means that make it possible to introduce and to distribute liquid $F_1$ that contains the reagents or liquid $F_2$ that contains the products and the excess reagents that have not reacted. Liquid $F_2$ can come from a distillation zone that is located above reaction zone Z.

The fluid that is introduced, $F_1$ or $F_2$, depends on the position of the reaction zone inside the distillation column and on its position relative to the distillation zones.

The means for introduction and distillation of fluids comprise at least one pipe 21 that is located, for example, approximately at the center of chamber 11. Said pipe 21 is connected to, for example, a zone 23a for distributing liquid, that is located below the catalyst bed. This distribution zone contains, for example, a liquid distribution device 23 that is presented in detail in FIGS. 5 and 6, whereby pipe 21 can contain orifices (FIGS. 5 and 6) for the liquid to pass toward the distribution zone.

At its upper portion, pipe 21 can contain a collecting unit that is well suited for optimizing the distribution and collection of the liquid in pipe 21 and inside a catalyst bed. This unit contains, for example, a pipe 51 and a zone 53 or overflow. In cases where catalyst 22 is saturated or clogged by the liquid that is introduced by pipe 21 and distributed by device 23, the presence of overflow 53 makes it possible to deflect the excess liquid toward a channel 18 for circulation of the liquid.

Catalyst bed 22 is kept in place with the aid of means 26, 27, such as Johnson type grids that are commonly used and whose characteristics can be similar to those that are described in Patent FR 2,737,131 of the applicant.

In the example that is given in FIG. 2, reaction zone Z is located between two distillation zones D, and the distribution of the liquid is done in the following manner.

Liquid $F_1$ or $F_2$ flows out on a plate 52 of upper distillation zone D that is located above the reaction zone and drops through pipe 21 to be distributed by distribution device 23 into catalyst bed 22. It circulates inside this bed in a rising manner. The liquid that contains the products and the excess reagents passes through upper Johnson grid 27, flows out over the latter up to wall 11b of the chamber, and overflows wall 11b into the channel for circulation of liquid 18 that is delimited by walls 11a, 11b and two consecutive walls 15. It flows out from top to bottom up to lower distillation zone D that is located below reaction zone Z and which is presented in detail below.

Figure 5:
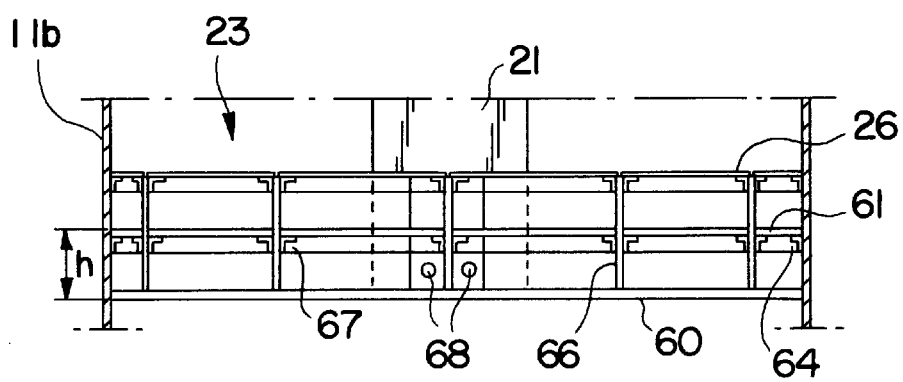
FIGS. 5 and 6 show an embodiment of a system for distributing fluid toward the reaction zone.
Figure 6:
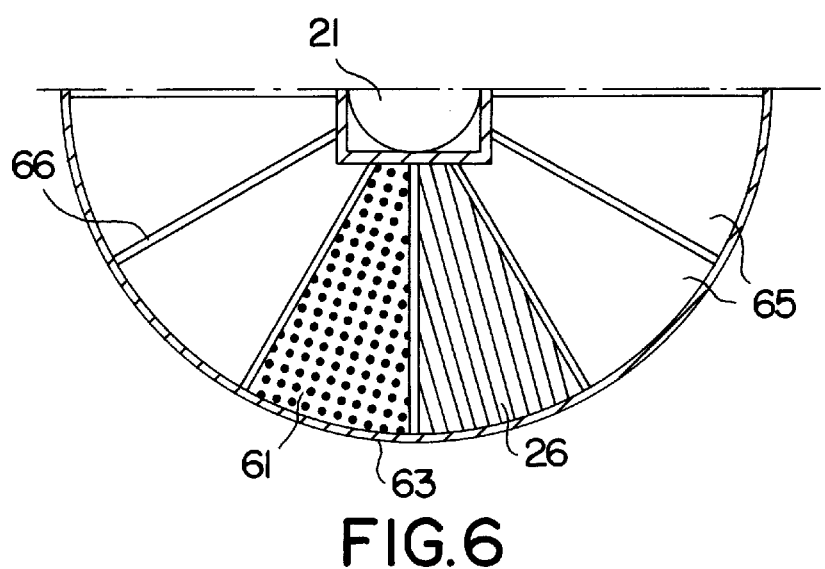

Distribution device 23 can be held by suitable means 24, 25, at the inner wall of chamber 11 to make it easy to connect and disconnect all of its elements that are described or else to individually inspect each of the elements that constitute it (FIGS. 5 and 6). To determine holding means 24, 25, it is possible to take into account the presence of downtake 21 and all of the elements whose weight may be placed on it.

Johnson grids 26, 27, which keep the bed from overflowing during operation, are linked to, for example, support beams 30, for positioning them or holding them relative to one of the elements of the reaction zone, for example, the wall of the chamber or else downtake 21. For this purpose, the downtake or the wall of the chamber is equipped with suitable means, for example, a raised edge 30, 29 or any other suitable mechanical means. The upper Johnson grid is located above catalyst bed 22 to leave enough room to allow the optional variation of the catalyst bed during the reaction (variation of volume).

Lower or upper distillation zone D that is described in this example is made of so-called "double-pass" distillation plates, i.e., through which the fluid to be separated circulates, for example, centrally and laterally, on the two sides that comprise the raised edge.

Distillation zone D comprises, for example, two distillation plates 33, 34 (upper plate and lower plate, considering the reaction zone that is located above), and a downtake 35. Upper plate 33, which communicates with channel 18 for circulation of the liquid that comes from the catalyst bed, has a diameter that is approximately equal to the inner diameter of the reactive distillation column. It can be equipped with baffles, not shown, and located close to the lower opening of the space of passage 18 whose function is in particular to quiet the turbulence of the liquid. The liquid falls onto this plate before passing through downtake 35 by overflowing over raised edge 36 toward lower plate 34. On its two outer sides, the lower plate comprises, for example, raised edges for overflow 37 to allow the passage of the liquid that results from the distillation toward another reaction zone, for example. The separated vapor is evacuated toward circulation channels 17 where it circulates in an upward manner.

Walls 11a and 11b of circulation channel 18 are positioned relative to upper plate 33 essentially to prevent vapor from passing into the channel for circulation of liquid 18.

The elements that form the distillation zone, the distillation plates and the essentially central downtake, can be readily detached from one another. For this purpose, they each comprise means that make it possible to hold them together while preserving the good mechanical behavior of the unit. At least one of the distillation plates, for example the upper plate that has a diameter that is approximately identical to that of the column, can be equipped with means 39 that are located on its periphery, coming, for example, to connect to elements 40 that are located on inside wall 5a of the reactive distillation column.

The size and geometry of the distillation plates are selected to allow the passage of the vapor, in this example upward through channel or channels 17 and that of the liquid toward a lower doublet, for example, or a distillation plate of the lower doublet.

Upper plate 33 of the distillation zone can be equipped with means that make it possible to hold and position it relative to the wall of the column, and a reference means that is located on, for example, its upper face to receive, for example, the lower edges of the wall that form the central downtake. In this way, all of the plates that form the distillation zone can be held with respect to one another, whereby the lower plate can receive at least some of the weight of a reaction zone that is located on it or optionally the weight of any other unit.

Without exceeding the scope of the invention, it is possible to use more than two distillation plates to carry out the distillation.

FIG. 4 shows a detail of the zone for hooking a doublet to wall 5 of reactive distillation column IV of FIG. 3.

In this example, which is by no means limiting, the reaction zone of the doublet is held by means 31, which come to be hooked on elements 32 that are integral with inner wall 5a of the reactive distillation column. Such an arrangement makes it possible to suspend the reaction zone. Elements 32 of the column can exist in the case of a column that is already designed or yet to be installed, depending on the needs of the customer. Elements 31 and 32 are adapted to support the entire weight of the reaction zone by itself or else the weight of this reaction zone and various fluids that pass through it, for example, when the chemical reaction is carried out.

The reactive distillation column that receives the doublet can be equipped with existing reference means, or they can be installed depending on the needs of the operator.

The basically liquid fraction that comes from the chemical reaction and comprises the products that come from the reaction and the remainder pours out toward distillation zone D that is located below reaction zone Z.

FIGS. 5 and 6 present a cutaway view and a view along a section of an embodiment of distribution device 23 of FIG. 2.

The zone for distributing the liquid is located below the lower Johnson grid.

The distribution space is made up of, for example, a lower airtight plate 60 above which is located, at a certain distance h, a perforated plate 61 (FIG. 6) that has dimensions that are approximately identical to those of airtight plate 60. It is possible to position several plates above one another between lower airtight plate 60 and Johnson grid 26. The perforated plate or plates are, for example, equipped with orifices 63, whose size, geometry, and number are selected as a function of the pressure drop that is to be obtained before the liquid passes through the catalyst bed. The airtight and perforated plates are held, for example, at pipe 21 by means that are known to one skilled in the art, or else held relative to the wall of the column that can be equipped with means 64 that receive the plate or plates.

In order to create distribution sectors that are independent of one another, a perforated plate that comprises several sectors 65 that are connected to one another is used in such a way as to form a plate whose diameter is approximately identical to that of the airtight plate. The various sectors are, for example, separated by beams 66 which extend up to airtight plate 60 and up to Johnson grid 26. The connection between these various elements is ensured by the beams and means 67 that make it possible to ensure the seal between the various distribution sectors.

Pipe 21 for introducing fluid comprises, at its lower end which is connected to the sectors for distributing liquid, one or more openings 68 which each communicate with one of sectors 65 for distributing fluid.

The liquid that comes in through pipe 21 and that is thus distributed via an opening into a zone that is located between the airtight plate, the perforated plate and a distribution sector. From a distribution sector, it circulates upward toward the catalyst bed by passing through the perforated orifices of plate 61 and lower grid 26.

The perforated plate is formed by, for example, a single piece or several parts that are joined to one another to form a perforated plate that is approximately identical in size to that of the airtight plate that forms the base of the distribution space.

The device according to the invention can be used in various balanced reactions, in the liquid phase, for which it is possible to isolate the reaction product by distillation under the temperature and pressure conditions under which the reaction is carried out, and particularly the alkylation reactions of aromatic hydrocarbons with suitable olefin, the reactions for isomerizing paraffins, the reactions for isomerizing olefins, or the production of butene-2 by hydroisomerization. Preferably, they are used more particularly in etherification reactions between an isoolefin (for example, isobutene or isopentene) and an aliphatic monoalcohol (for example, methanol or ethanol) to form the corresponding ethers. The conditions under which these reactions are carried out are well known to one skilled in the art. By way of example, however, the synthesis conditions of methyl tert-butyl ether are given below.

The conditions that are usually employed are generally a pressure of between 0.4 and 1.6 MPa, a bottom temperature of the reactive distillation zone, depending on the pressure selected, of between 110 and 170° C., and a top temperature of the reactive distillation zone, depending on the pressure selected, of between 40 and 90° C. In general, a flow rate relative to the distillate is kept between 0.5:1 and 5:1. By this process, it is possible to convert almost all the isobutene and to obtain MTBE with high purity, in general of at least 98 mol %. The batch that contains isobutene generally consists of a $C_4$ fraction (a hydrocarbon-containing batch that comprises in large part compounds that have 4 carbon atoms per molecule) that comes particularly from a unit for steam cracking, catalytic cracking, or dehydrogenation of isobutane. In a first reaction zone, it is brought into contact with methanol, under reaction conditions that are well known to one skilled in the art. This reaction, which is balanced, makes it possible to convert a portion of the isobutene (in general from 70 to 90%) into MTBE. This mixture that comes from this first zone is then processed according to the reactive distillation process of the invention or in the reactive distillation device according to the invention. The batch that contains unconverted isobutene and methanol is generally introduced just below the catalytic zone. An addition of methanol is generally introduced just above said zone. It is also possible to provide for introduction of this addition at several points that are distributed along the catalytic zone. The catalyst is placed in the catalytic zones of the reactive distillation zone as described above.

The examples that are provided in Patent FR 2,737,131 of the applicant can illustrate the use of the device according to the invention.

Since the various elements of the reaction zone and the distillation zone are of the modular type, i.e., easy to detach and independent of one another, they are arranged in such a way as to provide an optimum geometry to carry out the operation of catalyst reaction and distillation and to support possible batches and operating conditions, in particular stability optionally in pressure and/or temperature.

In addition, the means that make it possible to keep them together and to ensure their hooking relative to the distillation column in which they are inserted have characteristics that are selected to make it possible to ensure the mechanical stability of the grid-chamber-pipe unit, for example, under the action of the weight of the catalyst or optionally of other mechanical or thermodynamic stresses.

The elements that make it possible to use the device according to the invention in an existing column, for example in the case of revamping a unit, will be determined and adapted depending on the needs of the producer.

The reaction zone can be self-supported, i.e., it is equipped with necessary and sufficient elements that make it possible to put it on, for example, an inner raised edge of the wall of the column. The inner raised edge of the walls of the column may be divided into several raised edges that are distributed over the periphery of the column and may be preexisting or fixed, as required.

Without exceeding the scope of the invention, it is also possible to provide for various ways of introducing the fluid that contains the reagents at the catalyst bed.

It is possible, for example, to use a means of introduction such as the one described in Patent Application FR-2,737,131 of the applicant.

The way and form in which the reagents are introduced, for example, in the vapor phase or the liquid phase, and/or the direction in which the fluid that contains the reagents is introduced, for example, in the upward or downward direction inside the catalyst bed, are selected particularly as a function of the reaction that is carried out in the reaction zone. The fluid distribution system is adapted accordingly.

The catalyst can be located according to one of the arrangements that are described in one of the above-mentioned patents or patent applications of the applicant.

Likewise, without exceeding the scope of the invention, the column in which a doublet or one of the elements of a doublet is located and/or the design of distillation zones is used can conform to one of the embodiments that is described in the above-mentioned applications and patents of the applicants.

The example that is described above in connection with FIGS. 1 to 3 was provided for a fluid that contains reagents and passes through the catalyst bed from bottom to top but may, without exceeding the scope of the invention, be extended to circulation of the fluid from the top toward the bottom through the catalyst.

The elements and/or the doublets that are described above may, without exceeding the scope of this invention, be located inside a column other than a reactive distillation column, but also any other chamber in which it is possible to run a chemical reaction, which may or may not be balanced.

Because of the presence of hooking elements between the various elements that constitute the device, the doublet and/or the zones of reaction or distillation, it is conceivable to replace these elements independently or with minimum change in the device.

In this way, an independent doublet that can be formed, for example, by a reaction zone that is associated with at least one distillation zone that is located below and/or above the reaction zone is advantageously achieved.

The walls of the chamber and of the column are equipped with, for example, flaps, not shown, through which it is possible to insert additional pipes that can be used in particular for introducing one or more other fluids, for allowing the passage of catalyst during operations of replacing the latter without shutting down the column, and optionally for deflecting the fluid and preventing it from passing through the catalyst bed. The column where a doublet is installed is equipped with, for example, corresponding flaps which will make it possible to run the pipes through and to connect them to the outside.

When the reaction that is employed includes the presence of at least one gas reagent, the process according to the invention can comprise at least an introduction of said gas reagent, preferably hydrogen, for each catalyst bed of the catalytic zone.

It is possible, of course, to be able to go down and install in an existing column a cage that comprises all of the elements that make it possible to carry out the reaction operation and/or a doublet that makes it possible to carry out the reaction and separation operations. This approach makes it possible advantageously to reduce defective-part replacement operations inside a column or else to modify columns in such a way as to optionally adapt them to the needs of the producer.

The zones for rectification or drainage of the reactive distillation column are designed according to, for example, a method that is described in Patent FR 2,737,131.

It is also possible to provide for the collecting of liquid at the lower catalyst bed. The liquid can actually contain catalyst particles that have been entrained; the recovery of the particles is done outside of the column by filtration, whereby the liquid that is free of particles is sent back to the lower distillation zone.

The various positioning arrangements of the reaction and distillation devices inside a reactive distillation column that is described in Patent FR 2,737,131 of the applicant can also be used without exceeding the scope of this invention.

What is claimed is:

1. A modular device suitable for conducting at least one chemical reaction in the presence of a catalyst, said device comprising in combination:
   at least one reaction zone where the chemical reaction is carried out, whereby said zone comprises a chamber (11) where a catalyst bed that comprises catalyst (22) is located,
   means (21) for introducing at least one liquid fluid $F_1$ that comprises at least one reagent, whereby said means are located approximately in the center of said chamber (11), with the fluid being introduced without contact with the catalyst,
   one or more sections (18) for passage of a second fluid $F_2$ that comprises reagents and the products that come from the catalyst, whereby said fluid is liquid,
   one or more sections (17) for passage that allows the circulation of at least a third fluid $F_3$ that is gaseous,
   said sections (17, 18) for passage are dedicated to the passage of a fluid,
   at least one of said sections (17) for passage comprises at least one wall (11a) common with at least one of said sections (18) for passage, and at least one wall that is formed by a inner wall of a reactive distillation device or an auxiliary element, and at least one of said sections (18) comprising a second wall (11b)
   said sections (17, 18) for passage are longitudinally coaxial with at least a portion of the periphery of said chamber (11),
   and a horizontal plate (33) proximate the lower edges of said walls (11a) and (11b), the lower edge of said wall (11a) being closer to said plate 33 than the lower edge of said wall (11b).

2. A device according to claim 1, characterized in that said sections (18) for passage that are dedicated to the passage of the liquid fluid are formed by a double wall (11a, 11b, 15), whereby one of the walls is common to at least a portion of an outer wall of chamber (11).

3. A device according to claim 1, wherein said means for introducing a at least one liquid fluid ($F_1$) comprise a pipe (21) that is equipped with one or more orifices (68) that communicate with a distribution zone (23a) that is located below the catalyst bed.

4. A device according to any one of claims 1–3, wherein said device is in fluid communication with at least one distillation zone (D) via said sections (17, 18) for passage.

5. A method of synthesizing a tert-alkyl ether comprising catalytically reacting an olefin with an alcohol, in a column comprising the modular device according to one of claims 1–3.

6. A column comprising at least one modular device suitable for conducting at least one chemical reaction, in the presence of a catalyst said column comprising in combination:
   at least one reaction zone where the chemical reaction is carried out, whereby said zone comprises a chamber (11) where catalyst (22) is located,
   means (21) for introducing at least one liquid fluid $F_1$ that comprises at least one reagent, whereby said means are located approximately in the center of said chamber (11), with the fluid being introduced without contact with the catalyst,
   one or more sections (18) for circulation of a second fluid $F_2$ that comprises reagents and the products that come from the catalyst, whereby said fluid is liquid,
   one or more sections (17) for circulation that allows the circulation of at least a third fluid $F_3$ that is gaseous,
   said sections (17, 18) for circulation are dedicated to the passage of a fluid,
   at least one said sections (17) comprises at least one wall (11a) common with at least one of said sections (18), and at least one wall that is formed by an inner wall of a reactive distillation device or an auxiliary element, and at least one of said sections (18) comprising a second wall (11b),
   said sections (17, 18) are longitudinally coaxial with at least a portion of the periphery of said chamber (11), and
   at least one distillation zone (D), whereby said distillation zone (D) is in fluid communication with said reaction zone via sections (17, 18),
   wherein said distillation zone (D) comprises a horizontal plate (33) proximate the lower edges of said walls (11a) and (11b) the lower edge of said wall (11a) being closer to said plate (33) than the lower edge of said wall (11b).

7. A column according to claim 6, wherein said modular device is located between an upper distillation zone and a lower distillation zone.

8. A column according to claim 6, wherein said modular device is suspended on an inner wall (5a) of said column.

9. A column according to claim 8, wherein means (19, 20) are located between said modular device and said inner wall of the column to keep fluid $F_3$ from meeting fluid $F_2$.

10. A column according to one of claims 6 to 9, wherein said means of introduction (21) communicates with a distribution device (23) that is located below the catalyst, whereby said means (21) and said device (23) allow fluid $F_2$ or $F_1$ to circulate from a portion of the column above the catalyst and then through the distribution device.

11. A column according to claim 6, wherein fluid $F_2$ or $F_1$ circulates downward and wherein fluid $F_3$ circulates upward in said sections (17).

12. A method of synthesizing a tert-alkyl ether comprising catalytically reacting an olefin with an alcohol in a column according to one claim 6 through 9.

13. A modular device suitable for conducting at least one chemical reaction in the presence of a catalyst, said modular device comprising in combination:
   at least one reaction zone comprising a chamber (11) having a periphery and comprising a catalyst bed comprising catalyst (22),
   means (21) for introducing at least one liquid fluid $F_1$ comprising at least one reagent, said means being located approximately in the center of said chamber (11), said means (21) permitting the introduction of the liquid fluid without contact with the catalyst, one or more sections (18) for passage of a second fluid $F_2$ comprising reagents and products withdrawn from the catalyst bed, said fluid $F_2$ being a liquid, one or more sections (17) for passage permitting circulation of at least a third fluid $F_3$ that is gaseous, said sections (17, 18) for passage being dedicated to the passage of a fluid, wherein said sections (17, 18) are not in fluid communication, at least one of said sections (17) for passage comprising at least one wall (11*a*) common with at least one of said sections (18) for passage, and at least one wall formed by an inner wall of a reactive distillation device or an auxiliary element, and at least one of said sections (18) comprising a second wall (11*b*), said sections (17, 18) for passage being longitudinally coaxial with at least a portion of the periphery of said chamber (11), and a horizontal plate (33) proximate the lower edges of said walls (11*a*) and (11*b*), the lower edge of said wall (11*a*) being closer to said plate (33) than the lower edge of said wall (11*b*) and means (31) for removably retaining said modular device in said reactive distillation device.

14. A modular device suitable for conducting at least one chemical reaction in the presence of a catalyst said device comprising in combination:

at least one reaction zone where the chemical reaction is carried out, whereby said zone comprises a chamber (11) where a catalyst bed that comprises catalyst (22) is located, means (21) for introducing at least one liquid fluid $F_1$ that comprises at least one reagent, whereby said means are located approximately in the center of said chamber (11), with the fluid being introduced without contact with the catalyst, wherein said means comprise a pipe (21) that is equipped with one or more orifices (68) that communicate with a distribution zone (23*a*) that is located below the catalyst bed, wherein said distribution zone comprises at least one lower airtight plate (60) and at least one perforated plate (61), one or more sections (18) for passage of a second fluid $F_2$ that comprises reagents and the products that come from the catalyst, whereby said fluid is liquid, one or more sections (17) for passage that allows the circulation of at least a third fluid $F_3$ that is gaseous, said sections (17, 18) for passage are dedicated to the passage of a fluid, a section (17) for passage comprises at least one wall common with a section (18) for passage, and at least one wall that is formed by an inner wall of a reactive distillation device or an auxiliary element, said sections (17, 18) for passage are longitudinally coaxial with at least a portion of the periphery of said chamber (11).

15. A device according to claim 14, wherein said perforated plate comprises several sectors (65) for distribution of the liquid fluid, whereby said sectors are separated by means (66) and each of said sectors communicates with at least one opening (68) of pipe (21).

16. A device according to any one of claims 14 or 15, wherein said device is in fluid communication with at least one distillation zone (D) via said sections for passage (17, 18).

17. A method of synthesizing a tert-alkyl ether comprising catalytically reacting an olefin with an alcohol, in the column comprising a modular device according to claims 14 or 15.

18. A modular device suitable for conducting at least one chemical reaction in the presence of a catalyst, said device comprising in combination:

at least one reaction zone where the chemical reaction is carried out, whereby said zone comprises a chamber (11) where a catalyst bed that comprises catalyst (22) is located, means (21) for introducing at least one liquid fluid $F_1$ that comprises at least one reagent, whereby said means are located approximately in the center of said chamber (11), with the fluid being introduced without contact with the catalyst, one or more sections (18) for passage of a second fluid $F_2$ that comprises reagents and the products that come from the catalyst, whereby said fluid is liquid, wherein said means (21) is equipped with an overflow element (53) for preventing the clogging of the catalyst bed and for deflecting excess liquid into sections (18)

one or more sections (17) for passage that allows the circulation of at least a third fluid $F_3$ that is gaseous, said sections (17, 18) for passage are dedicated to the passage of a fluid, at least one of said sections (17) for passage comprises at least one wall common with at least one of said sections (18) for passage, and at least one wall that is formed by an inner wall of a reactive distillation device or an auxiliary element, said sections (17, 18) for passage are longitudinally coaxial with at least a portion of the periphery of said chamber (11).

19. A device according to claim 18, characterized in that said sections (18) for passage that are dedicated to the passage of the liquid fluid are formed by a double wall (11*a*, 11*b*, 15), whereby one of the walls is common to at least a portion of an outer wall of chamber (11).

* * * * *